United States Patent
Cyr et al.

(10) Patent No.: US 7,307,714 B2
(45) Date of Patent: Dec. 11, 2007

(54) APPARATUS AND PROCESS FOR DETECTING INCLUSIONS

(75) Inventors: David G. Cyr, Painted Post, NY (US); Christopher P. Daigler, Painted Post, NY (US); David R. Fladd, Summerville, SC (US); David C. Jenne, Hammond, NY (US); Albert R. Nieber, Corning, NY (US); Nikki Jo Russo, Gouverneur, NY (US); Paul J. Shustack, Elmira, NY (US)

(73) Assignee: Corning Incorporated, Corning, NY (US)

( * ) Notice: Subject to any disclaimer, the term of this patent is extended or adjusted under 35 U.S.C. 154(b) by 340 days.

(21) Appl. No.: 11/133,889

(22) Filed: May 20, 2005

(65) Prior Publication Data

US 2005/0259247 A1    Nov. 24, 2005

Related U.S. Application Data (60) Provisional application No. 60/573,317, filed on May 21, 2004.

(51) Int. Cl.
*G01N 21/88* (2006.01)

(52) U.S. Cl. .............................. 356/239.1; 356/239.8; 356/237.1

(58) Field of Classification Search ........ 356/400–403, 356/237.1–237, 239.1, 239.2, 239.3, 239.7, 356/338, 429, 128; 250/559.45, 559.46, 250/559.47, 559.49
See application file for complete search history.

(56) References Cited

U.S. PATENT DOCUMENTS

| | | | |
|---|---|---|---|
| 2,367,704 A | 1/1945 | Walker | 88/14 |
| 3,586,444 A | 6/1971 | Sproul et al. | 356/129 |
| 3,843,268 A | 10/1974 | Kaye | 356/246 |
| 3,857,637 A | 12/1974 | Obenreder | 356/120 |
| 4,049,350 A * | 9/1977 | Bruck | 356/30 |
| 4,136,961 A * | 1/1979 | Young, II | 356/239.1 |
| 4,178,103 A * | 12/1979 | Wallace | 356/336 |
| 4,645,337 A * | 2/1987 | Obenreder | 356/128 |
| 5,465,153 A * | 11/1995 | Ladewski | 356/601 |
| 5,627,638 A * | 5/1997 | Vokhmin | 356/124 |
| 5,790,247 A * | 8/1998 | Henley et al. | 356/237.1 |

(Continued)

FOREIGN PATENT DOCUMENTS

JP    11183392 A    10/1999

(Continued)

*Primary Examiner*—Sang H. Nguyen
(74) *Attorney, Agent, or Firm*—Robert P. Santandrea; Siwen Chen (57) ABSTRACT

Disclosed are process and apparatus for inspecting internal inclusions in internally transmissive substrates. The process involves applying a black coating to one major surface of the substrate, submerging the substrate in a refractive index-matching fluid, and scanning the substrate with a collimated light beam. The scattered light signals produced by the inclusions can be detected by the human eye or by using a light detector. By the use of index-matching fluid and the black coating, the signal-to-noise ratio of the process and apparatus are enhanced. A preferred black coating is one cured from an electron beam or photo polymerizable coating composition applied to the major surface. The process and apparatus are particularly suitable for inspecting internal inclusions in an internally transmissive substrate having considerable amount of surface defects or contoured surface that prevent it from inspection in a gas medium.

28 Claims, 2 Drawing Sheets

U.S. PATENT DOCUMENTS

| | | | |
|---|---|---|---|
| 5,945,462 A | 8/1999 | Salamon | 522/37 |
| 6,250,512 B1 | 6/2001 | Salamon | 222/402 |
| 6,388,745 B2 * | 5/2002 | Stevens et al. | 356/239.7 |
| 6,404,489 B1 | 6/2002 | Yu | 356/239.1 |
| 6,876,448 B2 * | 4/2005 | Imura et al. | 356/326 |
| 2001/0040678 A1 | 11/2001 | Stevens et al. | 356/239.7 |

FOREIGN PATENT DOCUMENTS

| | | |
|---|---|---|
| JP | 2001154206 | 6/2001 |
| JP | 2002060470 | 2/2002 |
| WO | WO02/53298 | 7/2002 |

* cited by examiner

FIG. 1
Amended

Fig. 4
New

US 7,307,714 B2

APPARATUS AND PROCESS FOR DETECTING INCLUSIONS

CROSS-REFERENCE TO RELATED APPLICATIONS

The present invention claims priority under 35 U.S.C. § 119 of U.S. provisional application Ser. No. 60/573,317 filed on May 21, 2004 and entitled "Apparatus and Process for Detecting Inclusions," which is relied upon and incorporated herein by reference in its entirety.

FIELD OF THE INVENTION

The present invention relates to apparatuses and processes for detecting small size inclusions in solid media such as bulk glass and plastic substrates. In particular, the present invention relates to detecting micron-size and submicron-size inclusions in bulk glass media having high surface roughness. The present invention is useful, for example, in detecting inclusions in lapped fused silica bulk substrates having high surface roughness.

BACKGROUND OF THE INVENTION

Many optical members and devices are required to be free of internal inclusions. For example, the optical devices used in modern photolithographic processes and equipment for the production of semiconductor products must be free of inclusions. Such inclusions could be small gas bubbles, refractory particles and platinum particles and the like introduced into the glass during the preparation process. The inclusions, in micron size or submicron size, are not acceptable in stepper lenses and photomask substrates. It is important that such inclusions be detected in the inspection process before a piece of glass bulk material is processed into the lens or photomask substrate. Inclusion detection in other transparent media, such as in bulk plastic material, for use as window panes, visors, or optical members, is also necessary for many applications.

However, detecting small (micron scale and submicron) inclusions in solid media, such as glass, has been a challenge. The difficulties associated with various practices are sensitivity, resolution, depth of focus, to name a few. Microscopy has the capability to detect inclusion down to the submicron range, yet it has an extremely narrow depth of focus and a small sampling area at high magnification. If used alone, these restrictions make it next to impossible to analyze bulk glass. Diffused reflection/scattering has been used to identify inclusion. After mapping their location, the inclusion can be further determined by microscopy. Nevertheless, the detection limit for the diffused reflection/scattering approach is about 5 microns and as low as 1 µm. In addition, the thickness of the glass is again somewhat restricted by the narrow depth of focus of the microscopy technique.

Small particles suspended in a fluid media, such as a liquid or gas, on the other hand, can be measured routinely by light scattering techniques. The differences between inclusions in a solid glass and particles suspended in a fluid are critical. One difference is that an inclusion in a glass is stationary. Its concentration level is normally very low, thus the signal intensity is so weak that it can hardly be distinguished from noise. Noise is the detected light that is not generated by scattering and/or reflection of the inclusion. In addition, the location of inclusions in glass would be valuable information. Due to the dynamic nature of the suspended particles in a fluid media, their location cannot be mapped.

U.S. Pat. No. 6,388,745 B2 and U.S. Patent Application Publication No. 2001/0040678, which are relied upon and incorporated herein by reference in their entirety, disclose an apparatus and a process for detecting inclusions in transparent sheets such as glass sheets. The apparatus includes a light source providing a primary light beam, a lens for focusing a majority of the scattered light generated by the inclusion, and a CCD array detector for detecting the focused signals. The lens has a light trap which blocks the primary light beam and prevents it from entering the detector to improve signal-to-noise ratio.

U.S. Pat. No. 6,404,489 B1, which is relied upon and incorporated herein by reference in its entirety, discloses another apparatus and process for detecting inclusions in transparent sheet. The apparatus comprises a laser source providing a primary collimated laser beam, at least one light trap positioned on an exterior surface of the sheet to be inspected and at least one detector for detecting the scattered light signals generated by the inclusions. The light trap blocks the primary laser beam and prevents illuminating the surface contaminants of the glass sheet. In one embodiment as disclosed in this patent reference, two light traps are used. The light detector as disclose in this reference can be a two-dimensional CCD array.

In general, the devices and methods in the above references were to be used for inspection of transparent glass articles having precision surfaces with a low rate of surface defects. The inspection light beam used in these devices enters into the substrates through the side surfaces without appreciable reflection loss and scattering. Moreover, the very few surface defects do not cause significant interference to the inspection of internal inclusions. For substrates having a large number of surface defects, these processes and instruments are not suitable. An example of substrates having a large number of surface defects are those lapped but not precision polished. Those substrates may have a high surface roughness such that when placed in the air, they appear diffuse because of light scattering at the surfaces. If the processes and instruments disclosed in the prior art references are used directly on these substrates, the collimated inspection light beam will be scattered significantly by the surface defects and the light scattering signals generated by internal inclusions will be drowned.

Of course, one way to inspect the internal inclusions of a substrate having large number of surface defects is to first precision polish the surfaces before inspection. This, however, is not always feasible. Besides, if internal inclusions can be detected and located before surface polishing of the substrate, substantial cost savings can be effected by avoiding the costly polishing of a defective product.

Therefore, there remains a genuine need of a method and an apparatus for inspecting the internal inclusions of substrates having considerable amounts of surface defects without the need of precision surface polishing.

The present invention satisfies this need.

SUMMARY OF THE INVENTION

According to one aspect of the present invention, it is provided a process for detecting internal inclusions in a solid internally transmissive substrate having a first major surface, a second major surface opposite to the first major surface and at least one side surface, the first and second major surfaces and/or the at least one side surface optionally comprising light scattering defects that prevent direct inspection of the solid substrate in a gas medium, comprising the following steps:

(i) applying a light-absorbing black coating on the second major surface;

(ii) placing the substrate having the black coating on the second major surface into an index-matching fluid having a refractive index matching that of the substrate;

(iii) providing a collimated light beam;

(iv) scanning the substrate by passing the collimated light beam through the index-matching fluid and the side surface and through the substrate;

(v) detecting, at a position on the side of the first major surface, light scattered by an internal inclusion, if present, when the collimated light beam is intercepted by the internal inclusion; and (vi) determining the presence/absence and/or location and/or size of the inclusion in the substrate.

The process of the present invention is equally applicable for inspecting internal inclusions of internally light transmissive substrates with surfaces having large or small number, or even no surface defects. However, the process of the present invention is particularly suitable for inspecting substrates having a large number of surface defects, such as those with surfaces having high roughness due to cutting or lapping. In a preferred embodiment of the process of the present invention, the collimated light beam is a laser beam. In a preferred embodiment of the process of the present invention, where the substrate comprises light scattering defects on the second major surface, in step (i), the black coating is applied in a manner such that it fills the defects. Where the surfaces of the substrate comprises large number of defects, it is preferred that the at least one side surface, or at least the surface through which the collimated light beam enters into the body of the substrate, is ground to a roughness of less than about 30 µm, preferably less than about 20 µm. In an embodiment of the present invention, where the substrate comprises multiple side surfaces, the side surfaces other than the side surface through which the collimated light beam enters into the body of the substrate, or at least the side surface opposite to the side surface through which the collimated light beam enters into the body of the substrate, are further coated with the black coating similar to the black coating applied to the second major surface of the substrate.

In one embodiment of the process of the present invention, in step (ii), the first major surface is placed above the second major surface, and step (v) is performed above the first major surface. Step (v) can be performed by a human eye, or by using an artificial light detector such as photo sensors normally used. It is preferred that the surfaces of the substrates are thoroughly cleaned before step (i) of the process of the present invention such that the surfaces are essentially free of light scattering or reflecting particle contaminants. Preferably, the substrate is placed in a black shroud during the inspection process.

In one embodiment of the process of the present invention, in step (iv), only the lower part of the incident side surface is scanned through, and the process further includes the following additional steps after step (vi):

(vii) removing the substrate from the index-matching fluid;

(viii) removing the black coating from the second major surface;

(ix) cleaning the substrate;

(x) switching the designation of the first major surface and the second major surface; and subsequently (xi) performing steps (i)-(vi), wherein in step (iv), the remaining part of the same incident side surface is scanned through.

The black coating applied to the second major surface of the substrate in the process of the present invention can be applied by spraying a black paint thereto. In a preferred embodiment of the process of the present invention, in step (i), the black coating is applied by the following steps:

(A) applying an electron beam or photo polymerizable coating composition on the second major surface; and (B) polymerizing the coating composition into a black coating by exposing it to electron beam or actinic irradiation.

It is preferred the black coating formed in step (B) fills in the defects, if any, of the second major surface.

In the process of the present invention for inspecting internal inclusions, it is preferred there is an additional step of (xii) at the end of the inspection cycle, removing the black coating from the second major surface. Preferably, the black coating is removed by peeling. Preferably, the black coating can be peeled off in large pieces. More preferably, the black coating can be peeled off in a single piece.

Another aspect of the present invention is an apparatus for detecting internal inclusions in a solid internally transmissive substrate having a first major surface, a second major surface opposite to the first major surface and at least one side surface, the first and second major surfaces and/or the at least one side surface optionally comprising light scattering defects that prevent direct inspection of the solid substrate in a gas medium, comprising:

a collimated light source providing a collimated light beam;

a vessel comprising black walls into which an index-matching fluid and the substrate can be placed, which has a transparent window fitted in one wall through which the collimated light beam enters into the vessel during inspection, wherein the transparent window has a flat polished external light incident surface and an optionally flat and polished internal surface; and optionally a light detector for detecting light scattered by inclusions in the substrate.

The apparatus of the present invention may further comprise an applicator for applying a black electron and/or photo polymerizable coating composition onto the second major surface of the substrate, and an electron beam or actinic irradiation source for curing the coating composition into a black coating. The optional light detector in the apparatus of the present invention may be, for example, a CCD array or a photodiode. The apparatus of the present invention may comprise a light beam modulator, such as one comprising a turning mirror, for scanning the collimated light beam through the substrate. The apparatus of the present invention may further comprise a signal analyzer, for calculating the position and/or size of the inclusion from the information of the light scattered by the inclusions detected by the light detector.

The present invention is useful, for example, in the inspection of internal inclusions in solid internally transmissive substrates, such as substrates made of plastic and inorganic crystalline or glass or composite materials thereof. Representative benefits of the present invention process and apparatus include, but are not limited to: (i) a high signal to noise ratio; (ii) ability to detect internal inclusions, with naked eyes, as small as 5 µm, preferably 2 µm in diameter; (iii) ability to detect internal inclusions with even smaller size (submicron size) when CCD or other light detectors are employed; (iv) capability of inspecting internal inclusions of substrates with surfaces having a large number of defects; (v) capability of inspecting internal inclusions of substrates with contoured surfaces; (vi) high sensitivity for inspecting internal inclusions near the surface regions; and (vii) safety advantage of the apparatus of the present invention because the use of the black coating and the confinement of the inspection light beam in a vessel reduces the possibility of human exposure to the intensive collimated light beam.

Additional features and advantages of the invention will be set forth in the detailed description which follows, and in part will be readily apparent to those skilled in the art from the description or recognized by practicing the invention as described in the written description and claims hereof, as well as the appended drawings.

It is to be understood that the foregoing general description and the following detailed description are merely exemplary of the invention, and are intended to provide an overview or framework to understanding the nature and character of the invention as it is claimed.

The accompanying drawings are included to provide a further understanding of the invention, and are incorporated in and constitute a part of this specification.

DETAILED DESCRIPTION OF THE INVENTION

As used herein, the first major surface means the uncoated major surface of the substrate during inspection. The second major surface means the coated major surface of the substrate during inspection. The scattered light signal produced by internal inclusions travels through the first major surface and partly reaches the detecting human eye or a light detector. As indicated infra, the same major surface of the two major surfaces may serve as the first major surface or the second major surface during the whole inspection process, or may serve as the first major surface during part of the inspection procedure, and as the second major surface during the other part of the inspection procedure.

Figure 2:
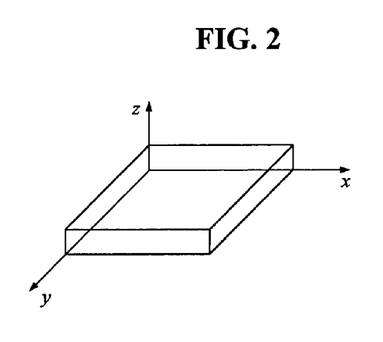
FIG. 2 is a schematic illustration of the geometry of one type of substrate that can be inspected for internal inclusion in the present invention process and apparatus.
Figure 3:
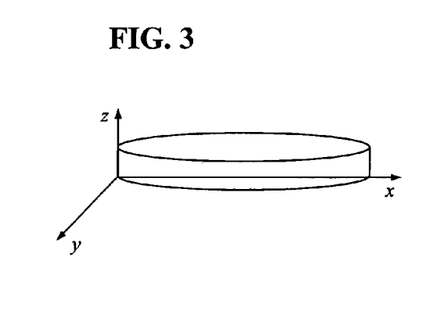
FIG. 3 is a schematic illustration of the geometry of another type of substrate that can be inspected for internal inclusion in the present invention process and apparatus.

Substrates to be inspected by using the process and apparatus of the present invention may take any shape, since once put into the index-matching fluid, the interface between the fluid and the substrate is substantially optically invisible. For example, the substrate can be rectangular. FIG. 2 illustrates a rectangular substrate in a (x, y, z) coordinate system. This substrate has two major surfaces parallel to the (x, y) plane, and four side surfaces parallel to the z axis. For another example, the substrate can be cylindrical. FIG. 3 illustrates a cylindrical substrate in a (x, y, z) coordinate system. This substrate has two major surfaces parallel to the (x, y) plane, and a single curved cylindrical side surface parallel to the z axis. The z axis generally corresponds to the thickness of the substrate in these two types of substrates.

It is to be understood that the designation of the major surfaces and the side surfaces are purely arbitrary. It may be beneficial in certain circumstances, for example, for the rectangular substrate of FIG. 2, to rotate the substrate along the x or y axis, such that the two major surfaces as illustrated in FIG. 2 parallel to the (x, y) plane become side surfaces, and two side surfaces as illustrated in FIG. 2 parallel to the z axis become the two major surfaces. However, it is generally preferred to designate the surfaces having the largest area as the major surfaces, especially in substrates having low rate of internal inclusions, in order to expedite the inspection process. A center line 201 parallel to the x axis of the front side surface is also illustrated in FIG. 2.

The cylindrical side surface of the substrate of FIG. 3 is illustrated as being intersected by the (x, z) plane into two equal halves (a front half and a back half) because the center axis of the cylindrical side surfaces lies in the (x, z) plane. For this type of substrate, scanning is deemed complete as long as the front half of the side surface is scanned.

As mentioned above, the process and the apparatus of the present invention can be used for inspecting internal inclusions of any internally transmissive substrate. All external surfaces of the substrate may have been precision polished and thus have very few defects and low surface roughness. These substrates can be inspected using methods and apparatus disclosed in the prior art references, discussed supra, as well. Some of the surfaces, especially if they have been precision polished, may have a transparent coating, such as antireflective coating. Some or all of the external surfaces of the substrate for inspection in the process and apparatus of the present invention may have considerable amount of defects and a high roughness thus they look opaque in the air because the defects cause a lot of light scattering. The substrates may be of any type of solid material, such as organic polymers and/or inorganic crystalline or glass materials. However, as mentioned above, the process and apparatus of the present invention are particularly advantageous for use in inspecting inclusions in substrates having surfaces with considerable amount of defects. The present invention will be particularly described and illustrated below in connection with the inspection of inclusions in glass substrates having surfaces with considerable amount of defects. It should be noted that the process and apparatus of the present invention are equally applicable for those other substrates mentioned above.

The manufacture of glass articles, especially fused silica glass articles, usually involves the production of a large glass boule first. The large boule is then cut into smaller boules and lapped before further processing into finished articles, e.g., optical members such as photomask substrate or stepper lens element. In the manufacture of large boule, inclusions such as particles and/or gas bubbles may be trapped inside. It is of great importance that those inclusions are not included in a photomask or stepper lens element. It is highly desirable to identify and locate the inclusions before they are precision polished, in large and small boules alike. However, lapped boules have high surface roughness that prevents the use of the inspection methods and apparatus available in the prior art discussed supra. The present inventors solved this problem by providing the present invention.

Figure 1:
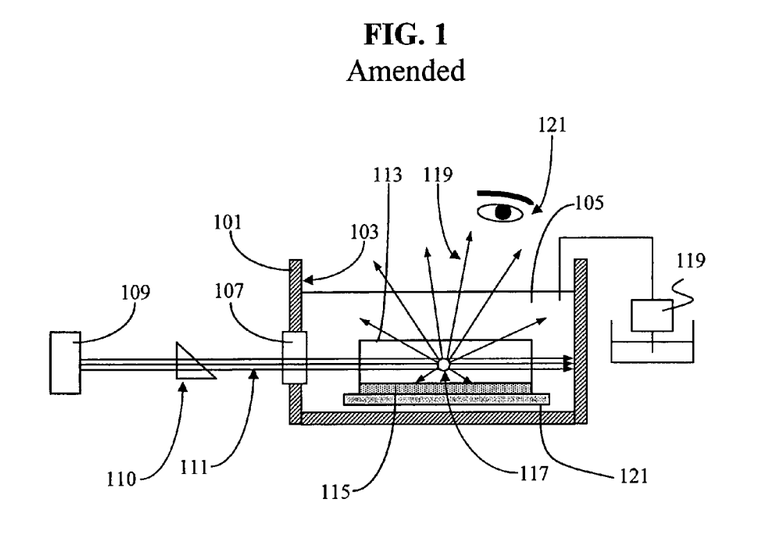
FIG. 1 is a schematic illustration of the cross-section of an embodiment of the apparatus of the present invention for inspecting internal inclusions when in use.

FIG. 1 is a schematic illustration of a preferred embodiment of the apparatus of the present invention for inspecting internal inclusions in an internally transmissive substrate when in use. This apparatus comprises a vessel 101 having inner black walls 103. It should be noted that the black walls 103 should include the inner surface of the bottom of the vessel as well. The wall can be made of black anodized aluminum, or covered with black rubber material or other black light-absorbing materials. Index-matching fluid 105 has been filled into the vessel 101. The apparatus of the present invention may comprise a pump 119 for introducing the index-matching fluid into and drawing the fluid out of the vessel 101. The index-matching fluid is preferably a non-toxic oil having low volatility. The fluid preferably has a stable refractive index during its life cycle and thus can be used for multiple inspection operations. The fluid is preferably stable when exposed to the air. The difference between the refractive index of the index-matching fluid and that of the substrate to be inspected is preferably less than 0.05, more preferably less than 0.01, still more preferably less than 0.005, most preferably less than 0.003, at the temperature of inspection and at the wavelength of the inspection light. Generally, if the side surface of the substrate has a very high surface roughness or is considerably uneven, a close index match, for example, an index difference less than 0.005, preferably less than 0.003, is required. The index-matching fluid 105 is preferably used for a plurality of cycles without the need of change or filtration. Afterwards, it is drawn out of the vessel 101 and filtered, reused and adjusted for refractive index, if necessary.

One wall of the vessel 101 is fitted with a transparent window 107. The window 107 is preferably made of a material having essentially the same refractive index of the substrate to be inspected. However, it is not required that the window 107 has essentially the same refractive index as the substrate to be inspected as long as the surfaces of the window 107 are reasonably flat and polished. Advantageously, the window 107 is made of the same material as in the substrate to be inspected.

The collimated light beam 111 enters into the vessel and the index-matching fluid 105 via the window 107. Thus, in order to maintain the light beam collimated when entering into the index-matching fluid 105, it is required the window 107 has a flat and polished external surface (the incident surface through which the collimated light beam enters the window 107) that essentially does not scatter the light beam. The window 107 may have an external surface having antireflective coatings to minimize reflection loss.

Preferably the collimated light beam is orthogonal to the external surface of the window 107 during the scan and the inspection process so that the sensitivity and resolution of the inspection within the bulk of the substrate is substantially the same. This can be done by raster scanning the beam across the external surface of the window 107 along the x and z axis while maintaining the beam perpendicular to the surface. This requires the window to have a size at least as large as that of the side surface of the substrate through which the substrate is to be inspected.

However, it is not required that the collimated light beam is always orthogonal to the external surface of the window 107 during the scanning and inspection process. For example, where a turning mirror is used to scan the light beam through the substrate within an incident angular range, the incident beam may enter the window at various angles not orthogonal to the external window of the window 107. If the incident collimated light beam is not orthogonal to the incident external surface, it will change its propagation direction and size when it enters the window 107 from a medium having a different refractive index, such as air, but will remain collimated after entering into the window 107. Where the incident light beam is scanned into the substrate within a large incident angular range, it is preferred that the external surface of the window 107 is not coated with antireflective coating because most antireflective coatings do not have as large an effective operation incident angular range.

If the window has essentially the same refractive index with that of the index-matching fluid, the inner surface (the surface through which the collimated light beam exits the window 107 and enters into the index-matching fluid 105) is not required to have a polished surface or an antireflective coating. However, since the refractive index of the index-matching fluid 105 and that of the window are not a perfect match, it is preferred that the inner surface of the window is polished to a low surface roughness to minimize scattering. Of course, if the window has a refractive index that differs considerably from that of the substrate to be inspected, which is acceptable, the inner surface of the window 107, like the external surface, must be reasonably flat and polished in order to maintain the light beam collimated when it exits the window and enters into the index-matching fluid.

The size of the window 107 is not critical to the present invention, as long as it permits a full and efficient scan of the intended scanning zone of the substrate to be inspected by the light beam.

The collimated inspection light beam is provided by a collimated light source 109 and a light beam modulator 110. The wavelength of the light beam is not critical. The collimated light source can be a halogen light, a laser generator, or other suitable light source. A highly collimated laser is preferred. The wavelength of the laser can be advantageously chosen to be in the most sensitive region of the human eye or the artificial light detector 121, depending on which is to be used for detecting the scattered light signal. For example, if the inclusions are to be detected by human eyes, it is preferred that the laser is a green laser, for example, of 532 nm, which is in the most sensitive region of the human eye. It is known that the human eye is about 5 times more sensitive to a 532 nm green light than to a He—Ne-red laser light. Thus, to achieve the same sensitivity and resolution, a substantially lower power of green light is required. Lower power of the inspection light beam brings about safety advantages. It is important to keep the power level of the light beam as constant as possible within the vessel in order to maintain the detection threshold. If the light beam is scanned across a large incident angular range, for example, by using a turning mirror, it is important that the laser beam is linearly polarized, and the orientation of the polarization is perpendicular to the external surface of the window. Otherwise, the laser power transmitted into the vessel will fall off quickly as the angle of incidence increases. With the polarization oriented as stated, the transmittance approaches 100% at Brewster's angle, ~62° incidence in either direction. Transmittance at 0° is around 96% (Fresnel).

The light beam modulator 110 may be integrated into the light source 109. The modulator functions to adjust the direction and/or size and/or shape of the light beam 111 such that the substrate can be scanned through the incident side surface completely, accurately and efficiently. The modulator 110 may include a turning mirror capable of back and forth vertical movement. The turning mirror can be advantageously a polygon mirror. The turning mirror can be a rotating mirror or an oscillating mirror. If a turning mirror is used to direct the light beam within an angular range, it is preferred that the mirror surface has an aluminum coating or, more preferably, a protected aluminum coating to allow high reflection over the range of incidence angles that the beam is scanning. One skilled in the art can also design the light source 109 and the modulator that can perform the scanning functions without the use of a turning mirror. The beam size and shape of the collimated light beam can be chosen by one skilled in the art to achieve quick yet accurate inspection. Preferably, to avoid hazardous exposure to the collimated light beam, especially a highly intensive laser beam, it is preferred that the light source and the light beam modulator are confined within a housing.

During the inspection, the substrate 113 to be inspected is submerged in the index-matching fluid. The substrate is placed with the first major surface facing upward and the second major surface facing downward. Note in FIG. 1, the second major surface has a black coating 115. The collimated light beam enters into the substrate 113 through an incident side surface. Understandably, if the incident side surface of the substrate 113 through which the laser beam enters into the substrate is a precision planar surface essentially without defect, the collimated light beam 111 will remain collimated after entering into the substrate 113, even if the index-matching fluid 105 is not present. However, in case the index-matching fluid is not present, if the incident side surface is not a planar surface (for example, if it is a contoured surface), or if the surface contains defects (such as a lapped but not polished surface), the collimated light source will be manipulated at the surface, and will no longer remain a collimated light beam after entering into the substrate. This will greatly reduce the signal-to-noise ratio of the apparatus because the light diffused at the surface may be detected by the human eye or the light detector as well. It is critical to maintain the inspection light beam collimated after entering the incident side surface of the substrate. With the presence of the index-matching fluid 105, light refraction at the interface between the index-matching fluid and the substrate is minimized, even if the incident side surface of the substrate is contoured or has a high roughness, thus the inspection light beam will remain substantially collimated and unaltered when entering into the substrate 113.

The collimated light beam 111 then travels through the substrate. If an inclusion 117 is present, during the scanning operation, it will intercept the collimated light beam. Because the inclusion 117 usually has a different refractive index than the substrate material, it will scatter the intercepted inspection light. The scattered light 119 will travel through the substrate and the index-matching fluid. A part of the scattered light will be detected. A part of the scattered light will reach the second surface, where it is absorbed by the black coating. A part of the scattered light will travel to the walls of the vessel, where they are absorbed as well. The absorption by the black coating on the second major surface and the vessel wall can help to improve the signal-to-noise ratio of the apparatus of the present invention.

The scattered light signals can be detected by the human eye or an artificial light detector, as mentioned supra. In case the signal is to be detected by the human eye, the apparatus of the present invention does not require an artificial light detector. The artificial light detector for use in the present invention may be any type of photosensor, such as a photo camera, a CCD, photodiodes and other opto-electronic light detecting equipment. Only one light detector 121 is shown in FIG. 1. However, it is to be understood that multiple light detectors, e.g., a CCD array, may be used. The detector is placed at the side of the first major surface, where the light scattered by the inclusions can be detected. The use of multiple detectors at different locations can improve the sensitivity of the apparatus, and can help determine the location of the inclusion.

In the embodiment illustrated in FIG. 1, only one collimated light beam is used. Indeed, in order to improve inspection speed and to pinpoint the location of the inclusion, multiple light beams may be used. One embodiment contemplated is an apparatus in which two light beams, orthogonal to each other, are used to scan the substrate simultaneously or at different times. The two beams may be split from a single beam or be generated from different light sources. In the latter case, the two beams can have the same or different wavelength. In another contemplated embodiment, the apparatus of the present invention uses one fixed collimated light beam, and a motor is equipped that can rotate the substrate, by an angle, for example, of 90°. After the inspection of the whole substrate from one side surface or one direction, the motor rotates the substrate, and the substrate is subject to another scanning cycle, but from a different side surface or a different angle. These multiple scanning solutions can help increase the sensitivity of the apparatus, as well as determine the exact coordinates and size of the inclusion.

In addition to rotation, the substrate may be capable of vertical back-and-forth movement to aid the scan of the substrate and determination of the location of inclusions in the substrate. This can be achieved by placing a substrate stage (121 in FIG. 1) in the vessel of the apparatus of the present invention, wherein the stage 121 is equipped with mechanisms, such as motors, capable of rotating the stage 121 in the (x, y) plane and/or driving the stage up and down along the z axis.

In an automated apparatus, the light detectors are preferably connected directly with a signal analyzer, such as a computer. The computer may also advantageously be connected with the light source, the light beam modulator, and the index-matching fluid pump, to control them and/or to obtain information thereof. The computer can determine the presence/absence of any inclusion, calculate the size and coordinates of the inclusion inside the substrate based on, among others, information of the scattered light detected by the single or multiple light detector, information of the collimated light beam available from the light source and/or the light beam modulator, information about the substrate (such as geometry, size, etc.), and information of the position of the substrate if the substrate is rotated during the inspection or moves vertically as describe above. The computer may adjust the shape, size and intensity of the collimated light beam, change the status of the light beam modulator, turn on the pump on or off in pumping the index-matching fluid in and out of the vessel, turn on or off the motor that moves the substrate in the index-matching fluid, etc. These controls may be exercised automatically by the computer according to instructions from the computer operator, and/or in response to sensors placed in the individual components of the apparatus, and/or in response to internal instructions stored in the computer. In a simpler version of the apparatus of the present invention, a human operator performs all or part of the functions of the computer. He may manually control the apparatus. He may detect the scattered light using his naked eyes and determine the position of the inclusion.

To aid the determination of the location of the inclusions, it may be desired to mark the surfaces, especially the major surfaces with reference marks such as grid lines. Such reference marks are desirably detectable and recognizable by the light detector or the human eye, with or without the aid of supplementary illumination of the surfaces. For example, grid lines can be marked by simply using a pencil and a ruler. However, the marking and detection of the grid lines should not substantially compromise the sensitivity of inclusion detection.

Usually, if an inclusion is detected in the substrate and its location is determined, the part having the inclusion will be cut off. Sometimes the size information of the inclusion is useful in determining the size of the part that should be cut off. In addition, the size of the inclusion, as well as the composition, rate and distribution thereof within the substrate, are all useful information for the optimization of the manufacture process of the substrate. Therefore, sometimes it is necessary to use additional equipment, such as a microscope, to determine the size of the inclusion. The use of microscope is greatly facilitated by the location information of the inclusions in the substrate by using the process and apparatus of the present invention.

Of course, the inspection process of the present invention should advantageously be carried out in a setting where interference by ambient light is minimized, for example, in a dark room. Also, in order to prevent the interference of inspection by dust, it is preferred the whole inspection, including the surface cleaning steps, are conducted in semi clean room or standard clean room environment.

The presence of the black coating on the second major surface is essential for the inclusion inspection process of the present invention. The present inventors have found that small gas bubbles or other particulates tend to exist in the index-matching fluid. Some of the bubbles may rise and adhere to the second major surface if the surface is not coated with the black coating 115. In addition, the major surfaces may comprise particles and other contaminants. These bubbles and contaminants, on or near the major surfaces, may scatter light and generate noise and reduce detecting sensitivity. Furthermore, the defects of the major surfaces, if any, may scatter light, even in the presence of an index-matching fluid, because the index match cannot be perfect. Because the collimated light beam covers a relatively large area, for example, a 2 mm diameter area, when inspecting the substrate portion near the major surfaces, it is inevitable that the beam will pass through the near-surface region inside the substrate and/or outside of the substrate in the index-matching fluid. All these factors lead to a reduced signal-to-noise ratio if a black coating does not exit when inspecting the near surface region. The black coating, non-reflective and non-transmissive to the inspection light, prevents these detrimental noises from arising near the second major surface or absorbs them, thus greatly enhancing the signal-to-noise ratio of the process of the present invention. Indeed, the present inventions have found that, the inspection of internal inclusions near the uncoated first major surface is subject to detrimental noise signal generated by the defects, contaminants and/or bubbles close to or adhered to the first major surface when the inspection light beam passes near the first major surface, either within the substrate or partly through the index-matching fluid.

Therefore, though for certain substrates the inspection of internal inclusions can be done by a single inspection operation of the whole incident side surface including the near second major surface region, as well as the near first major surface region, the sensitivity of the inspection with regard to the internal inclusions near the first major surface is not optimized. As mentioned supra, the present invention thus also includes an inspection process having two inspection stages. In the first stage, the collimated light beam is scanned through the lower part, e.g., approximately the lower half, of the scanning incident side surface. For example, for a substrate illustrated in FIG. 2, in the first stage, the light beam is scanned through the half of the incident side surface under the center line 201, and the area slightly over the center line. Thus, the net result of the first stage is the completion of scanning of, for example, 70% of the of the incident side surface, preferably about 65% of the incident side surface. After the completion of this first stage inspection, the substrate is taken out of the index-matching fluid, the black coating is peeled off the second major surface and the substrate is thoroughly cleaned. The designations of the first major surface and the second major surface are then switched, i.e., the original first major surface becomes the second major surface and the original second major surface becomes the first major surface, for the identification purpose in the second stage inspection. Then the second stage of inspection process begins with application of the black coating onto the new second major surface, followed by placing the substrate into the index-matching fluid, providing the collimated light beam, scanning through the remaining part, e.g., the lower half of the incident side surface, and the area slightly over the center line of the incident side surface, and determination of the presence/absence, coordinates and size of the internal inclusions. The net result of the both the first and second stages combined is that the whole substrate is scanned for inclusions. Certain area along the center line of the side surface may have been scanned twice in this method. In this process, by avoiding scanning the substrate near a major surface without a black coating on it, improves the overall sensitivity and signal-to-noise ratio of the process.

For the black coating to function as so intended, it is desired that essentially no particle or gas bubble is trapped between the second major surface and the black coating. Thus cleaning of the second major surface before application of the coating is very important. Indeed, in order to reduce noise caused by surface contaminants, it is required that all surface of the substrates are thoroughly cleaned before inspection. The cleaning may include a step of acid cleaning, detergent cleaning with or without the aid of ultrasonic energy, deionized water rinsing, drying, and the like. The coating should adhere to the second surface during the inspection process without delaminating, and the coating should preferably fill in the defects on the second major surface. After inspection of the substrate is completed, and before the substrate is used or further finished before end use, the black coating will be removed. Preformed black coatings, such as black plastic films, may be useable for precision polished surfaces. However, for surfaces having large number of defects, such as lapped surfaces having high roughness, a preformed coating applied to the surface, such as by electrostatic force, will invariably not be able to fill in the defects, thus leaving voids or gas bubbles between the film and the surface, which will cause interference to the inclusion detection, especially when the collimated light beam scans through the near second major surface region. Thus, for substrates having high surface roughness or otherwise having large number of defects, a black coating on the second surface applied freshly from liquid state is desired, so that the defects will be filled in upon curing or hardening of the coating.

Traditionally used non-reflective, non-transmissive permanently adherent coatings, deposited by painting followed by baking, may be employed as long as it does not negatively affect further processing of the substrate, especially if the inspection process involves painting only one major surface. For example, where a portion of the substrate including the second major surface will be cut away after inclusion inspection, and the presence of the black coating does not negatively affect the cutting process, such permanent coatings may be employed. However, a temporary coating with easy removability is preferred in many applications, especially where the inspection process involves coating both major surfaces at different stages and removing the coating at the end of the first inspection stage. Desirably, the black coating can be removed by simple peeling, preferably in large pieces, more preferably in a single piece, from the second major surface at the end of the inspection, while still maintain enough adherence to the second major surface during the inspection when immersed in the index-matching fluid.

Simple, commercially available black spray paints can be used for the black coating in the process of the present invention. Multiple layers of coating may be applied to achieve the desired thickness. However, there are a number of problems associated with using black spray paints for this purpose. Standard spray paints can pose a fire and inhalation safety hazard due to their containing volatile, flammable solvents. They also can take an unacceptably long time to dry. This can be addressed using drying ovens, IR lamps, etc., but at considerably extra cost or space consumption.

Additionally, after drying and the inclusion analysis are performed, removal of most spray paints can be done by scraping the coating off with a razor blade. This process is messy and it creates static electricity which makes the paint shards stick to the glass. The scraping process is also time consuming, can damage the glass surface, and is unsafe due to the potential for hand laceration hazards.

Several of these problems are addressed if water-based black coatings are used. These coatings eliminate the fire and inhalation safety hazards and, at least one of them, Stripaway 4420 from General Chemical Corporation (Detroit, Mich.) will peel off a glass substrate in one piece. However, this material cures upon water evaporation so drying time is dependent on temperature, humidity, air movement and thickness of coating. At best, with force dried air at 100° F., the coating can cure in less than 10 minutes. Non-drying assisted coatings take several hours to dry and the vendor recommends that the coating is applied on weekends or late afternoons to give the coating time to dry. Similar materials are available from Simco Coatings, Inc. (Belle Chasse, Ind.).

Thermoplastic, hot-melt materials have been used for this purpose but the materials must be heated to their melting point to apply. This makes them hard to paint on and spray application is not possible.

P. A. Salamon in U.S. Pat. No. 5,945,462 and U.S. Pat. No. 6,250,512 uses a water based, UV curable material as a temporary protective coating for precision surfaces such as glass lenses. The compositions can be pigmented. However, coating removal requires either using pressure sensitive adhesive tape or soaking in a warm water detergent solution. These compositions also require a water removal drying step in addition to a photocuring step.

T. Jaworek et al. in WO 2002053298 presents a method of producing a coated substrate, e.g., glass, by applying a coating agent containing carbon black or other UV absorbers, and curing the layers by UV radiation. They found that by varying the concentration of the carbon black or UV absorbers in the layers, a gradient in the degree of cure forms resulting in the formation of a lacquer on the substrate with different physical properties, e.g., hardness, elasticity, etc. This is undesirable in this application because a lower degree of cure would present a safety hazard because it would result in the handling of substrates coated with uncured or incompletely cured materials.

S. Nakamura et al. in JP2002060470 presents compositions useful for inks or coatings that comprise (a) compounds having $\geq 2$ epoxy groups, (b) compounds generating acids by absorbing radiation, (c) pigments and/or metal powders, and (4) unsaturated compounds having $\geq 1$ OH and $\geq 1$ unsaturated bond. An example is presented where carbon black is added to the composition and it is coated onto a glass plate and cured by UV radiation to give a completely cured product with no surface tackiness and improved adhesion. No mention is made of any possibility of using this type coating for substrate inclusion analysis or the potential peelability of the coating off of the substrate after cure.

S. Ogasawara et al, in JP2001154206 presents radiation curable compositions and their use in spacers of liquid crystal display devices. The compositions comprise (a) copolymers of unsaturated carboxylic acids and/or anhydrides, unsaturated group containing epoxy compounds and other unsaturated monomers, (b) polymers bearing unsaturated groups, (c) radiation polymerization initiators and, (d) colorants. An example is presented where carbon black is added to the composition and it is spin coated onto a glass surface, dried, and then cured with UV light through a photo-mask to give a spacer film of 5 µm thickness with good light blocking property and resistance to heat and rubbing. The composition required a 5 hour at 70° C. drying step because it contained propylene glycol monomethyl ether acetate solvent.

Although the above black coatings can be used for the process of the present invention, they all have tradeoffs.

Figure 4:
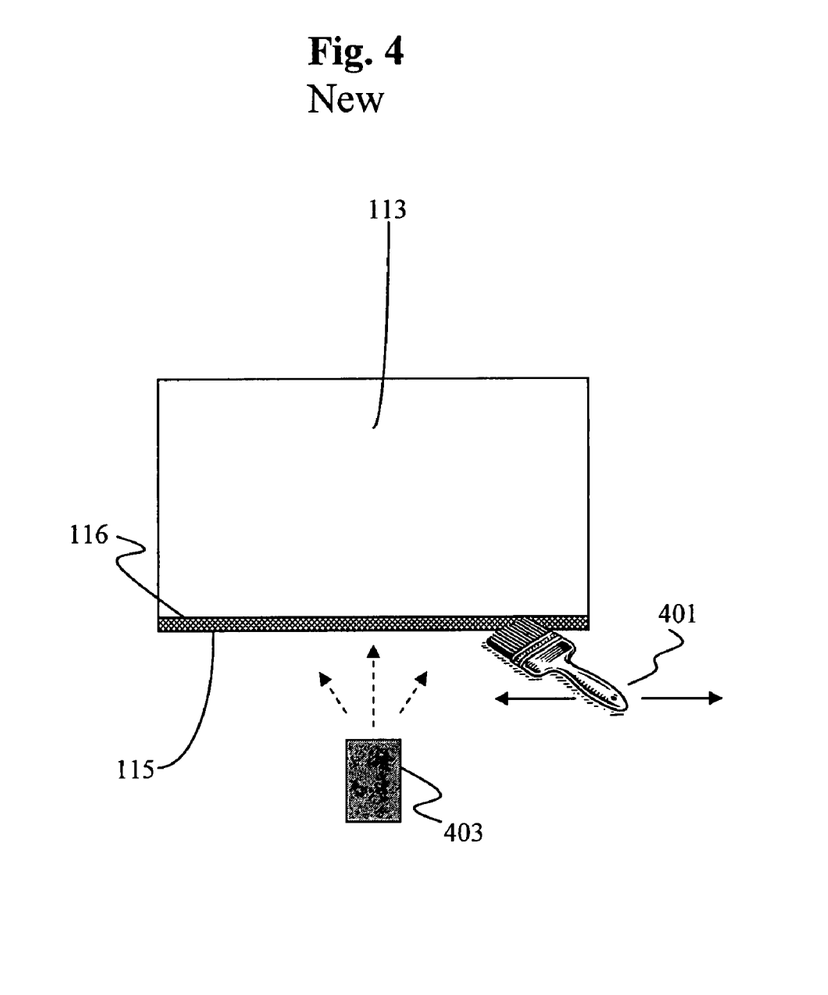
FIG. 4 is a schematic illustration of application of a photo polymerizable coating onto a surface of a substrate.

The present inventors have developed a electron beam and/or photo curable black coating (115 in FIG. 4) to apply to a glass surface (116 in FIG. 4) such that, after cure, the coating 115 is removable by simple peeling from the glass surface 116. Many photocurable compositions may potentially be used with a prerequisite being that they do not contain water or solvents. The compositions also must cure in a fast time ($\leq 10$ minutes), preferably $\leq 5$ minutes, most preferably $\leq 1$ minute. The coating must be able to be applied by typical paint application procedures like brushing (401 in FIG. 4), rolling, spraying, dipping, screen printing, etc. After cure, the coating 115 must be opaque and non-reflective to the inspection light. Several layers can be applied but it is preferable to reach opacity in as few layers as possible, preferably one. Preferably, the cured black coating 115 has a thickness between 10-500 µm, more preferably between 15-400 µm, most preferably between 20-300 µm. If the coating is too thin, it will not be easy to peel off in large pieces or in a single piece, and it will not have the required light absorption capability. If the coating is too thick, it will require too much time to apply and dry, and it will be difficult to cure completely because the pigments usually absorbs the actinic irradiation used for curing the coating, leading to poor adhesion to the glass surface. The coating 115 should have sufficient adhesion to glass to enable the maintenance of adhesion during a soak in room temperature refractive index-matching oils for several days. However, the adhesion to glass should be low enough to enable easy removal (preferably by simple peeling) of the black layer. The black layer should also possess sufficient flexibility and cohesiveness to enable a peel-type removal from the glass. The peeled coating should ideally come off in one piece or, acceptably, in a minimum number of pieces. It is also desired that the components of the coating, when placed in the index-matching fluid, will substantially not be leached out and alter the composition, color and/or refractive index of the index-matching fluid.

In summary, the black coating developed by the inventors allows the facile application of a black coating to a surface of a glass object by brushing, dipping, rolling, spraying, screen printing, etc., and curing said coating with actinic light or electron beam. The curing (drying) of the black coating occurs in seconds to a few minutes on exposure to the actinic radiation or electron beam. Thus the black coating on the second major surface is easy to apply. The black coating eliminates optical interference from said glass surface and thus enables inclusion analysis to be performed on the glass object. After analysis, the black coating can be easily removed by simple peeling from the glass surface. The materials contain no volatile solvents so they obviate the hazards of flammability and the inhalation safety issues associated with these liquids. The materials have a very fast drying time because there is no need to evaporate off solvents or water in order to dry. This facilitates manufacturing throughput.

A preferred embodiment of the process of the present invention uses an electron beam (403 in FIG. 4) and/or photo polymerizable coating (115 in FIG. 4) that comprises a urethane acrylate based oligomer, a mono-functional acrylate monomer having about 10-30 carbon atoms, a photoinitiator and black pigment. The urethane acrylate based oligomer can be, for example, aliphatic or aromatic. The black pigment can be introduced by black ink products commercially available. The content of the black pigment in the coating composition should be sufficiently high to impart non-transmissive properties to the cured black coating on the second major surface having a reasonable thickness. However, as noted supra, if the pigment content is too high, it may absorb the actinic radiation, causing prolonged curing time, incomplete cure and hence poor adhesion to the glass surface.

The apparatus of the present invention may further include an applicator for applying the black coating composition to the second major surface and an electron beam or actinic radiation source for curing the black coating composition. One of ordinary skill in the art can choose the equipment, according to the teaching supra regarding the coating composition and the cured coating.

EXAMPLE 1

The following composition in TABLE I was prepared by adding the following ingredients into a stainless steel container. The container was placed on a hotplate and the composition was mixed with a stainless steel mixing blade at ~600 rpm until the mixture reached ~60° C. The composition was mixed at 600 rpm for one hour at 60° C. After cooling to room temperature the composition was ready for application.

TABLE I

| | |
|---|---|
| 31.00% | Photomer 6891 An aliphatic urethane acrylate oligomer(Cognis Corp. Ambler, PA) |
| 25.00% | Aronix M111 ethoxylated nonyl phenol acrylate (Toagasei Chemical Industry Co., Tokyo Japan.) |
| 4.00% | Irgacure 1800 Photoinitiator blend (Ciba Geigy Corp., Terrytown, NY) |
| 40.00% | DSM Cablelite ® 751 Black UV curable optical fiber ink (DSM Corp., Des Plaines, IL) |

Photomer 6891 is a viscous and flexible oligomer. Aronix M111 has the following general formula where on average n≈1.4.

This composition was applied to a surface of a glass substrate using a paint brush. The black-painted glass substrate was passed on a conveyor belt under a Fusion Systems 300 W/ in "D" type UV curing lamp at 20 ft/min (UV dose=1100 mJ/cm$^2$). The black coating was about 5 mils thick and was opaque to visible light. An inclusion analysis quality control test was successfully performed on the black-coated glass substrate. This test includes a soak of the black-coated glass substrate in refractive index-matching fluid. The black coating was easily removed by gently lifting an edge of the coating up with a knife or razor blade, then pulling the lifted edge with fingers so as to peel the black layer up off the glass, essentially, in one piece. The viscosity of the composition was 1300 cPs.

EXAMPLE 2

The following composition in TABLE II was prepared as in Example 1.

TABLE II

| | |
|---|---|
| 28.00% | Photomer 6891 |
| 22.00% | Aronix M-111 |
| 6.00% | Speedcure EDB (Ethyl-4-(dimethyl amino) benzoate from Aceto Corp. Lake Success, NY) |
| 4.00% | FirstCure BD-3 (Proprietary maleimide blend from Albemarle Corp., Pascagoula, MS) |
| 40.00% | DSM Cablelite ® 751 Black UV curable optical fiber ink (DSM Corp., Des Plaines, IL) |

This composition was drawn down onto a 4"×4"×0.7 mm thick glass plate using a 3 mil Bird applicator. The ~3 mil thick black film was cured with a Greenspot UV curing unit. The lightguide from the Greenspot UV curing unit was suspended at 2" above the black film. The UV exposure time was 99.99 sec. The black film cured completely dry to touch and can easily be peeled off of the glass substrate in one piece. The experiment was repeated using a 6 mil Bird applicator to draw down a ~6 mil black film onto the same size glass plate. The film was UV cured using the same exposure protocol. The film cured completely dry to the touch and easily peeled off of the glass substrate in one piece. An inclusion analysis quality control test was successfully performed on the black-coated glass substrate.

The black coating composition of this example requires smaller fluence of an actinic radiation to cure. Thus it does not require the use of expensive UV light source and is easier to cure than the composition of Example 1.

It will be apparent to those skilled in the art that various modifications and alterations can be made to the present invention without departing from the scope and spirit of the invention. Thus, it is intended that the present invention cover the modifications and variations of this invention provided they come within the scope of the appended claims and their equivalents.

What is claimed is:

1. A process for detecting internal inclusions in a solid internally transmissive substrate, the process comprising the following steps:
   (i) providing the substrate, the substrate having a first major surface, a second major surface opposite the first major surface, and at least one side surface, wherein at least one of the first major surface, second major surface, and the at least one side surface optionally comprise light scattering defects that prevent direct inspection of the solid substrate in a gas medium;
   (ii) applying a light-absorbing non-transmissive black coating on the second major surface;
   (iii) placing the substrate having the black coating on the second major surface into an index-matching fluid having a refractive index matching that of the substrate;
   (iv) providing a collimated light beam;
   (v) scanning at least part of the substrate by passing the collimated light beam through the index-matching fluid and the side surface and through the substrate;
   (vi) detecting, at a position on the side of the first major surface, light scattered by an internal inclusion, when the collimated light beam is intercepted by the internal inclusion; and
   (vii) determining and storing the presence of the internal inclusion and at least one of location and size of the internal inclusion in the scanned part of the substrate.

2. A process in accordance with claim 1, wherein in step (iv), the collimated light beam is a linearly polarized laser beam, the laser beam passes through a window abutting the index-matching fluid into the index-matching fluid, the window has a flat polished incident external surface, and the polarization of the laser beam is oriented perpendicular to the external surface of the window.

3. A process in accordance with claim 1, wherein the substrate comprises light scattering defects on the second major surface, and in step (ii), the black coating is applied in a manner such that the black coating fills in the defects.

4. A process in accordance with claim 1, wherein the substrate comprises light scattering defects on the at least one side surface.

5. A process in accordance with claim 1, wherein the substrate is thoroughly cleaned before step (ii) such that the surfaces are essentially free of light scattering particle contaminants.

6. A process in accordance with claim 1, wherein the at least one side surface is ground to a surface roughness of less than about 20 μm.

7. A process in accordance with claim 1, wherein the substrate comprises multiple side surfaces, and at least the side surface opposite to the incident side surface at which the collimated light beam enters the substrate is coated with a black coating.

8. A process in accordance with claim 1, wherein the substrate is placed in a black shroud.

9. A process in accordance with claim 1, wherein in step (v), only the lower part of the incident side surface is scanned through, and the process includes the following additional steps after step (vi):
   (viii) removing the substrate from the index-matching fluid;
   (ix) removing the black coating from the second major surface;
   (x) cleaning the substrate;
   (xi) switching the designation of the first major surface and the second major surface; and subsequently
   (xii) performing steps (ii)-(vii), wherein in step (v), the remaining part of the same incident side surface is scanned through.

10. A process in accordance with claim 1, wherein in step (ii), the black coating is applied by spraying a black coating composition to the second major surface.

11. A process in accordance with claim 1, wherein in step (ii), the black coating is applied by the following steps:
   (A) applying an electron beam or photo polymerizable coating composition on the second major surface; and
   (B) polymerizing the coating composition into a black coating by exposing it to electron beam or actinic irradiation.

12. A process in accordance with claim 11, wherein in step (ii)(B), the polymerized black coating fills in the defects on the second major surface.

13. A process in accordance with claim 11, wherein in step (ii)(B), the coating polymerizes and dries within 10 minutes.

14. A process in accordance with claim 11, wherein in step (ii)(A), the coating composition comprises black pigment.

15. A process in accordance with claim 11, wherein in step (ii)(A), the polymerizable coating composition comprises an urethane acrylate based oligomer, a monofunctional acrylate monomer having 10-30 carbon atoms, a photoinitiator and a black pigment.

16. A process in accordance with claim 1, further comprising the step of
   (xiii) at the end of the inclusion inspection cycle, removing the black coating from the second major surface.

17. A process in accordance with claim 16, wherein in step (xiii), the black coating is removed by peeling it off.

18. A process in accordance with claim 17, wherein in step (xiii), the black coating is peeled off in large pieces.

19. An apparatus for detecting internal inclusions in a solid internally transmissive substrate the apparatus comprising:
   a collimated light source providing a collimated light beam;
   a vessel comprising black inner walls into which an index-matching fluid and the substrate can be placed, which has a transparent window fitted in one wall through which the collimated light beam enters into the vessel during inspection, wherein the transparent window has a flat polished external light incident surface and optionally a flat polished internal surface, and wherein the substrate has a first major surface, at least one side surface, and a second major surface opposite the first major surface, the second major surface having a light-absorbing, non-transmissive black coating applied thereto; and
   a light detector for detecting light scattered by internal inclusions in the substrate.

20. An apparatus in accordance with claim 19, wherein the transparent window fitted in one wall of the vessel has essentially the same refractive index of the substrate to be inspected.

21. An apparatus in accordance with claim 19, further comprising:
   an applicator for applying at least one of a black electron beam and photo polymerizable coating composition onto the second major surface of the substrate; and
   an electron beam or actinic irradiation source for curing the coating composition into a black coating.

22. An apparatus in accordance with claim 19, further comprising a pump for filling the index-matching fluid into the vessel and drawing the fluid out.

23. An apparatus in accordance with claim 19, wherein the light detector is a CCD array or a photodiode.

24. An apparatus in accordance with claim 19, further comprising a light beam modulator for scanning the collimated light beam into the substrate.

25. An apparatus in accordance with claim 19, further comprising a substrate stage equipped with mechanism capable of at least one of rotating the stage and moving the stage up and down.

26. An apparatus in accordance with claim 19, further comprising a signal analyzer connected with the light detector for determining the presence of the internal inclusion and at least one of location, and size of the internal inclusion.

27. An apparatus in accordance with claim 26, wherein the signal analyzer is a computer connected with the light source, a light beam modulator, and an optional motor for moving the substrate in the index-matching fluid, for obtaining information therefrom and exercising control thereof.

28. An apparatus in accordance with claim 19, wherein the collimated light source provides a linearly polarized collimated laser beam, and the polarization of the laser beam is oriented perpendicular to the external surface of the window.

* * * * *